(12) United States Patent
Fosaaen (10) Patent No.: US 11,274,591 B2
(45) Date of Patent: *Mar. 15, 2022

(54) RESISTIVE BASED NOX SENSING METHOD AND APPARATUS

(71) Applicant: Kerdea Technologies, Inc., Greenville, NC (US)

(72) Inventor: Ken Ervin Fosaaen, Winterville, NC (US)

(73) Assignee: Kerdea Technologies, Inc., Greenville, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/930,739

(22) Filed: Jul. 16, 2020

(65) Prior Publication Data

US 2020/0347771 A1 Nov. 5, 2020

Related U.S. Application Data

(63) Continuation of application No. 16/080,876, filed as application No. PCT/US2017/021319 on Mar. 8, 2017, now Pat. No. 10,760,466.

(Continued)

(51) Int. Cl.
*F01N 11/00* (2006.01)
*G01N 27/16* (2006.01)
*G01N 33/00* (2006.01)

(52) U.S. Cl.
CPC ............ *F01N 11/002* (2013.01); *F01N 11/00* (2013.01); *G01N 27/16* (2013.01);

(Continued)

(58) Field of Classification Search
CPC .. F01N 11/00; F01N 11/002; F01N 2560/026; F01N 2560/06; G01N 27/16;

(Continued)

(56) References Cited

U.S. PATENT DOCUMENTS 4,770,760 A 9/1988 Noda et al.
4,927,517 A 5/1990 Mizutani (Continued)

FOREIGN PATENT DOCUMENTS

JP H03249555 A 11/1991
KR 20110123558 A 11/2011
WO 2011093975 A2 8/2011

*Primary Examiner* — Anthony Ayala Delgado
(74) *Attorney, Agent, or Firm* — Coats + Bennett, PLLC (57) ABSTRACT

Nitrous oxide (NOx) sensors and related methods and systems for use with combustion processes. The NOx sensor uses metal oxide semiconductors. The NOx sensor may have two sensing circuits that share a common electrode. The sensing circuits are differentiated by having different porous catalytic filter coatings protecting the metal oxide semiconductors: one sensing circuit has a porous catalytic filter coating that contains a Noxcat material (rhodium, ruthenium, cobalt, palladium, or nickel), while the porous catalytic filter coating of the other sensing circuit is substantially free of Noxcat material. The two sensing circuits are simultaneously exposed to the exhaust gases at a common macro location. The NOx level may be determined based on a difference in resistance between the two sensing circuits and a temperature of the NOx sensor.

20 Claims, 7 Drawing Sheets

Related U.S. Application Data (60) Provisional application No. 62/312,537, filed on Mar. 24, 2016.

(52) U.S. Cl.
CPC .... *G01N 33/0037* (2013.01); *F01N 2560/026* (2013.01); *F01N 2560/06* (2013.01); *Y02A 50/20* (2018.01); *Y02T 10/40* (2013.01)

(58) Field of Classification Search
CPC ........... G01N 33/0037; G01N 27/4067; G01N 27/4071; G01N 27/4076; Y02A 50/245; Y02T 10/47
See application file for complete search history.

(56) References Cited

U.S. PATENT DOCUMENTS

| | | | |
|---|---|---|---|
| 5,974,787 A | 11/1999 | Lemire et al. | |
| 6,012,282 A | 1/2000 | Kato | |
| 6,592,732 B1* | 7/2003 | Komachiya | G01N 27/419 204/426 |
| 6,695,964 B1* | 2/2004 | Ando | G01N 27/4074 204/425 |
| 8,586,394 B2 | 11/2013 | Fosaaen | |
| 8,959,987 B2 | 2/2015 | Fosaaen | |
| 2003/0066519 A1 | 4/2003 | Wachsman et al. | |
| 2004/0149595 A1* | 8/2004 | Moore | F01N 11/007 205/784.5 |
| 2008/0149499 A1* | 6/2008 | Ding | G01N 27/4065 205/783.5 |
| 2008/0169190 A1* | 7/2008 | Raghurama | G01N 27/12 204/400 |
| 2009/0223820 A1* | 9/2009 | Ishiguro | G01N 27/4065 204/424 |
| 2011/0168557 A1 | 7/2011 | Park et al. | |
| 2011/0186446 A1 | 8/2011 | Fosaaen | |
| 2012/0247186 A1* | 10/2012 | Sanjeeb | G01N 27/127 73/31.05 |
| 2014/0130779 A1 | 5/2014 | Fosaaen | |
| 2014/0360875 A1* | 12/2014 | Nolte | G01N 27/4075 204/424 |
| 2015/0083703 A1* | 3/2015 | Yazawa | G01N 27/4067 219/209 |
| 2016/0077044 A1 | 3/2016 | Arkenberg et al. | |
| 2016/0186695 A1* | 6/2016 | Dudar | F02M 25/0809 73/40.5 R |
| 2016/0204270 A1* | 7/2016 | Yamazaki | H01L 51/0512 257/43 |
| 2017/0074191 A1* | 3/2017 | Kim | F01N 3/2066 |
| 2017/0284999 A1* | 10/2017 | Maric | G01N 33/0047 |
| 2019/0033248 A1* | 1/2019 | Arkenberg | G01N 27/4162 |

\* cited by examiner

RESISTIVE BASED NOX SENSING METHOD AND APPARATUS

RELATED MATTERS

This application is a continuation of U.S. application Ser. No. 16/080,876, filed 29 Aug. 2018, which was the National Stage of International Application No. PCT/US2017/021319, filed 8 Mar. 2017, and claims the benefit of U.S. Provisional Application No. 62/312,537, filed 24 Mar. 2016, the entire disclosures of each of which are incorporated herein by reference.

BACKGROUND

This application is related to nitrous oxides sensors, methods of using nitrous oxides sensors, and related systems for use with combustion processes, for example in internal combustion engines and burner systems.

Nitrous oxides often form in internal combustion engines and burner systems under high temperature conditions. These are primarily NO, $NO_2$ and $N_2O$, and are collectively referred to as NOx. NOx formation is a particular issue in diesel engines, which run leaner and at higher compression ratios than typical spark ignition engines. These nitrous oxides, when released to the atmosphere, may combine with moisture to form nitric acid, leading to adverse health and environmental consequences. To combat this issue, modern engines and burner systems may be equipped with selective catalytic reduction systems which trap the NOx then react them with ammonia ($NH_3$) to form $N_2$ and $H_2O$. This ammonia is typically introduced into the system in the form of urea ($CO(NH_2)_2$), which converts to ammonia when heated in the exhaust stream. Nitrous oxide sensors are used to control the performance of such systems. These nitrous oxide sensors are placed after the NOx trap (typically a Selective Catalytic Reduction (SCR) catalyst), and once NOx is detected, the system is triggered to purge the trap using the urea. These nitrous oxide sensors should be durable and be capable of detecting NOx in the 1 to 2000 ppm range, and not experience cross sensitivities to other gasses ($H_2$, CO, sulfur and sulfur compounds, phosphorus and phosphorous compounds, etc.). Many NOx sensors on the market today are electrochemical sensors based on ion conductor technology; such NOx sensors have not proven satisfactory for all situations.

As such, there remains a need for alternative type of NOx sensors, and related systems and methods.

SUMMARY

This application is related to NOx sensors, methods of using NOx sensors, and related systems for use with combustion processes, for example in internal combustion engines. In particular, the application relates to NOx sensors that that have metal oxide semiconductor-based sensor portions, and related systems/methods. The NOx sensor may be used to sense NOx levels when exposed to exhaust gases of a combustion process.

In general, the NOx sensor may have two sensing circuits that share a common electrode. The sensing circuits contain the same metal oxide semiconductor material, but are differentiated by having different porous catalytic filter coatings thereon: one sensing circuit has a porous catalytic filter coating that contains a nitrous oxide catalyzing or "Noxcat" material (e.g., rhodium, ruthenium, cobalt, palladium, or nickel), while the porous catalytic filter coating of the other sensing circuit is substantially free of the Noxcat material. The two sensing circuits are simultaneously exposed to the exhaust gases at a common macro location. The NOx level can be determined based on a difference in resistance between the two sensing circuits and the temperature of the NOx sensor. The difference in resistance between the two sensing circuits is a result of the different amount of oxygen that the respective metal oxide semiconductor materials are exposed to due to the catalyzing action of the Noxcat material containing catalytic filter coating. The NOx values may be used to control an operation of the exhaust control system, such as triggering a purging of the NOx trap (e.g., providing urea/ammonia thereto) when the NOx level exceeds a threshold.

In one aspect, a nitrous oxide sensor has a substrate; a first oxygen sensing circuit affixed on a first side of the substrate; and a second oxygen sensing circuit affixed on the first side of the substrate. The first oxygen sensing circuit comprises a first sensing electrode; a common electrode; and a first metal oxide semiconductor portion electrically bridging a first physical gap between the first sensing electrode and the common electrode. The second oxygen sensing circuit comprises a second sensing electrode; the common electrode; and a second metal oxide semiconductor portion electrically bridging a second physical gap between the second sensing electrode and the common electrode. A first catalytic filter layer is disposed over the first metal oxide semiconductor portion, with the first catalytic filter layer comprising a Noxcat material. The Noxcat material is one of rhodium, ruthenium, cobalt, palladium, or nickel. A second catalytic filter layer is disposed over the second metal oxide semiconductor portion, with the second catalytic filter layer being substantially free of the Noxcat material. The first and second metal oxide semiconductor portions are disposed in spaced relation to each other such that there is a gap between the first and second metal oxide semiconductor portions. The first and second catalytic filter layers are disposed in spaced relation to each other. The first and second oxygen sensing circuits are configured to provide similar resistances when subjected to an environment free of nitrous oxide, but to provide substantially different resistances when subjected to an environment containing nitrous oxide(s).

In a second aspect, a nitrous oxide sensor includes a substrate; an electrically conductive common electrode mounted on a first side of the substrate; an electrically conductive first sensing electrode mounted on the first side of the substrate in spaced relation to the common electrode; and an electrically conductive second sensing electrode mounted on the first side of the substrate in spaced relation to the common electrode. The common electrode is disposed between the first and second sensing electrodes. The first sensing electrode and the common electrode are configured to form a first comb structure, and the second sensing electrode and the common electrode are configured to form a second comb structure. A first metal oxide semiconductor layer is disposed over the first comb structure and forms a first semiconductor bridge between the first sensing electrode and the common electrode. A second metal oxide semiconductor layer is disposed over the second comb structure and forms a second semiconductor bridge interconnecting the second sensing electrode and the common electrode. The first and second metal oxide semiconductor layers are spaced from each other. A first catalytic filter layer is disposed over the first metal semiconductor oxide layer, and a second catalytic filter layer is disposed over the second metal oxide semiconductor layer. The first catalytic filter layer comprises a Noxcat material and the second catalytic filter layer is substantially free of Noxcat material.

In a third aspect, a nitrous oxide sensor assembly includes the nitrous oxide sensor of the first aspect and/or the second aspect. In addition, the nitrous oxide sensor assembly includes a first voltage divider operatively connected to the first oxygen sensing circuit, and a second voltage divider operatively connected to the second oxygen sensing circuit, and processing circuitry. The processing circuitry is operative to: a) determine a first voltage drop associated with the first oxygen sensing circuit, the first voltage drop proportional to a resistance of the first oxygen sensing circuit; b) determine a second voltage drop associated with the second oxygen sensing circuit, the second voltage drop proportional to a resistance of the second oxygen sensing circuit; c) determine a temperature of the sensor; and d) determine if a purge of a NOx trap associated with a combustion process is needed by determining if a difference between the first voltage drop and the second voltage drop is greater than a first threshold. The first threshold may advantageously be based on the determined temperature of the nitrous oxide sensor. If the nitrous oxide sensor includes a heater portion, such as disposed on a second side of the substrate, the processing circuitry may be operative to determine the temperature of the nitrous oxide sensor by determining a voltage drop across a resistor disposed in series with the heater portion. In some sub-aspects, the processing circuitry is further operative to trigger a purge of the NOx trap in response to determining that the difference between the first voltage drop and the second voltage drop is greater than the first threshold.

In a fourth aspect, any NOx sensor disclosed herein may be used to detect nitrous oxide in exhaust from a combustion process. Such a method may include exposing the NOx sensor to the exhaust from the combustion process. The NOx sensor may have first and second oxygen sensing circuits that share a common electrode; wherein the first oxygen sensing circuit comprises a first metal oxide semiconductor portion in contact with the common electrode; wherein the second oxygen sensing circuit comprises a second metal oxide semiconductor portion in contact with the common electrode. The method includes passing some of the exhaust through a first catalytic filter layer to reach the first metal oxide semiconductor portion. The method also includes simultaneously passing some of the exhaust through a second catalytic filter layer to reach the second metal oxide semiconductor portion. The method includes at least partially converting nitrous oxide in the exhaust to oxygen while passing through the first catalytic filter layer prior to reaching the first metal oxide semiconductor portion, but in parallel nitrous oxide in the exhaust is not converted to oxygen while passing through the second catalytic filter layer to reach the second metal oxide semiconductor portion. The method also includes determining a temperature of the NOx sensor. The method also includes determining a nitrous oxide level in the exhaust based on a resistance differential between the first oxygen sensing circuit and the second oxygen sensing circuit, and the determined temperature. The first and second oxygen sensing circuits are configured to provide similar resistances when subjected to an environment free of nitrous oxide, but to provide substantially different resistances when subjected to an environment containing nitrous oxide(s). The process may continue by comparing the resistance differential to a threshold, and triggering a purging of the NOx trap (e.g., providing urea/ammonia thereto) when the determined NOx level exceeds the threshold.

The various aspects discussed above may be used alone or in any combination. The various apparatus disclosed herein may operate according to any combination of various methods disclosed herein, and vice versa. Further, the present invention is not limited to the above features and advantages. Indeed, those skilled in the art will recognize additional features and advantages upon reading the following detailed description, and upon viewing the accompanying drawings.

DETAILED DESCRIPTION

In one or more aspects, the present application is directed to a method of sensing NOx levels using a resistive based NOx sensor exposed to exhaust gases of a combustion process, and related devices and systems. In exemplary embodiments, the NOx sensor may have two sensing circuits that share a common electrode. The sensing circuits contain the same metal oxide semiconductor material, but are differentiated by having different porous catalytic filter coatings thereon: one sensing circuit has a porous catalytic filter coating that contains a nitrous oxide catalyzing or "Noxcat" material, while the porous catalytic filter coating of the other sensing circuit is substantially free of the Noxcat material. The term Noxcat material, as used herein, means any one of the following materials: rhodium, ruthenium, cobalt, palladium, or nickel, which are all class VIII elements in the periodic table of elements, and which act as catalysts to convert NOx to $N_2$ and $O_2$ at exhaust gas temperatures. The two sensing circuits are simultaneously exposed to the exhaust gases at a common macro location. The NOx level is determined based on a difference in resistance between the two sensing circuits. The sensed NOx level may be used to control an operation of the exhaust control system, such as triggering a purging of the NOx trap (e.g., providing urea/ammonia thereto) when the NOx level exceeds a threshold.

In one or more aspects, the sensor element is composed of a dielectric substrate onto which a platinum (or other suitable material) resistor is applied. This resistor can either be used as a means of measuring the temperature of the sensor element in a passive state due to the strong linear relationship between the resistance and the temperature, or (preferably) it can be used to control the temperature of the sensor element to a narrow value by adjusting the applied voltage; in this case it would function as a heater.

In one or more aspects, also applied to the ceramic substrate, advantageously on the opposite side, is a refractory (ex: platinum, palladium, or other suitable material) conductor consisting of at least three discrete electrodes. One of these electrodes is a common electrode, which forms two intermeshing combs with the other electrodes. One or more metal oxide semiconducting (MOS) materials are applied over these combs to form respective semiconductor bridges. The MOS materials may be an n-type MOS (ex: $TiO_2$) and/or a p-type MOS (ex: $Cr_2O_3$). Both materials require thermal energy (heat) to convert them from essentially dielectric materials to semiconducting materials with the following distinction: a) the resistivity of n-type semiconductors increases with increased oxygen exposure, and b) the resistivity of p-type semiconductors decreases with increased oxygen exposure. Porous coatings overlay these MOS materials. The porous coatings contain various catalytic materials to enhance responsiveness and/or protect the sensitive MOS material from contaminants and harmful deposits.

In one or more aspects, the MOS material and geometry used on each comb is advantageously the same with respect to material and geometry. The intention is that the combs would be held at essentially the same temperature due to their proximity to each other, and they would otherwise respond to the exhaust gasses to which they are exposed to in the same way with respect to their resistance if not for a difference in their respective porous catalytic coatings. The porous coating over one of MOS materials contains a Noxcat material (e.g., rhodium), whereas the porous coating over the other MOS material does not contain the Noxcat material. The purpose of the Noxcat material is to convert NOx to $N_2$ and $O_2$. As a result, the oxygen to which the MOS materials is exposed is therefore different, resulting in a different resistance, with the amount of the resistance difference depending upon the temperature, geometry of the sensing materials, electrodes, etc. Under these conditions, the resistance measurement difference is indicative of the presence of NOx, since the extra oxygen came from the conversion of NOx to $N_2$ and $O_2$. With an n-type MOS material the resistance of the Noxcat material catalyzed portion will be higher than the non Noxcat material bearing portion, while for p-type semiconductors, the Noxcat material bearing portion will have a lower resistance than the non-Noxcat material bearing portion.

Figure 5:
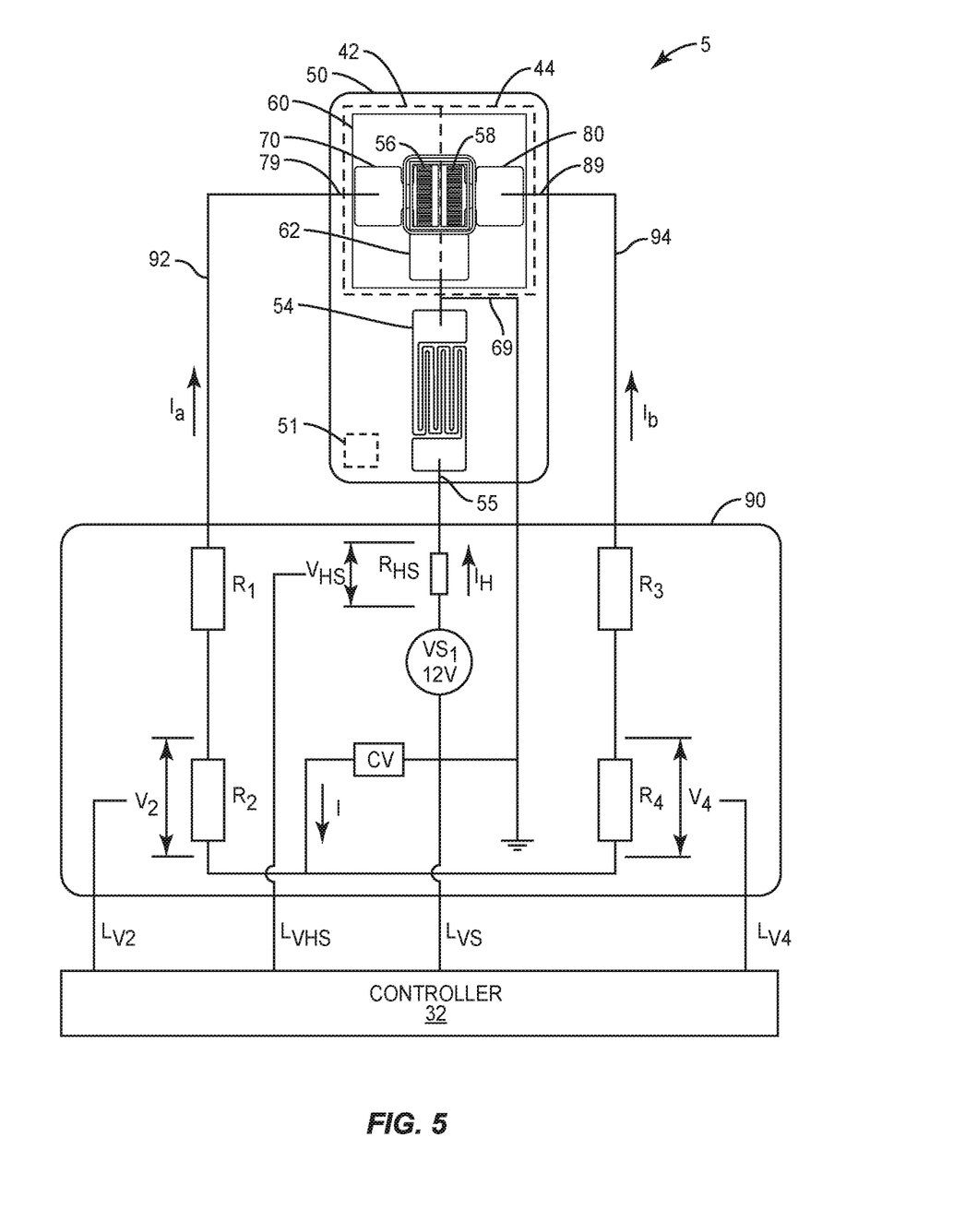
FIG. 5 shows a simplified schematic of the NOx sensor of FIG. 3 connected to a controller via a connecting circuit.

In one or more aspects, measurement of the resistance difference can be carried out in various ways including the following: Each leg of the sensor is placed in series with two resistors of known value (a voltage divider) and a fixed DC voltage (example 5 VDC) is applied across the circuit as shown in FIG. 5. The voltage drop across one of the two resistors in each leg is indicative of the resistance of the sensor element portion, which, in turn, is indicative of the state of the exhaust gas for that portion of the sensor, and the difference in the resistance is indicative of the presence of NOx in the exhaust gas.

By heating the NOx sensor and exposing it to the exhaust stream, the NOx sensor's resistance ranges will change according to the element temperature as well as the oxygen and NOx content of the gas to which it is exposed. The element temperature can be controlled by adjusting the voltage to the heater to hit a target heater resistance (calculated from applied voltage and measured current).

In one or more aspects, the more complete system is comprised of a sensor containing the sensor element described above (the three electrodes, the MOS material bridges, the catalytic layers, and the optional heater), which is packaged in a housing that is durable enough for the exhaust system environment, circuitry housed in the electronic control unit (or intermediate box) connected to the NOx sensor's heater and oxygen-sensitive MOS portions of the element, and a logic system to convert the range and differences in resistance along with temperature information to a NOx value.

The NOx sensor and accompanying circuitry described herein has applicability for single and multiple combustion chamber (piston, rotary, etc.) spark ignition (SI) as well as compression ignition (diesel and HCCI) engines and burner systems (boilers, heaters, etc.) where detection of NOx is important to the emissions management control system. However, for simplicity, the discussion herein may generally be in the context of an NOx sensor for a small displacement gasoline powered internal combustion engine, but it should be understood that the NOx sensor(s) disclosed herein may be used in other internal combustion engine applications, such as hydrogen powered engines, other hydrocarbon powered engines, diesel engines, Homogeneous Charge Compression Ignition (HCCI) engines, and Reactivity Controlled Compression Ignition (RCCI) engines. Further, the disclosed method(s) may be used with other combustion processes, such as, for example, those found in furnaces, boilers, and water heaters.

Figure 1:
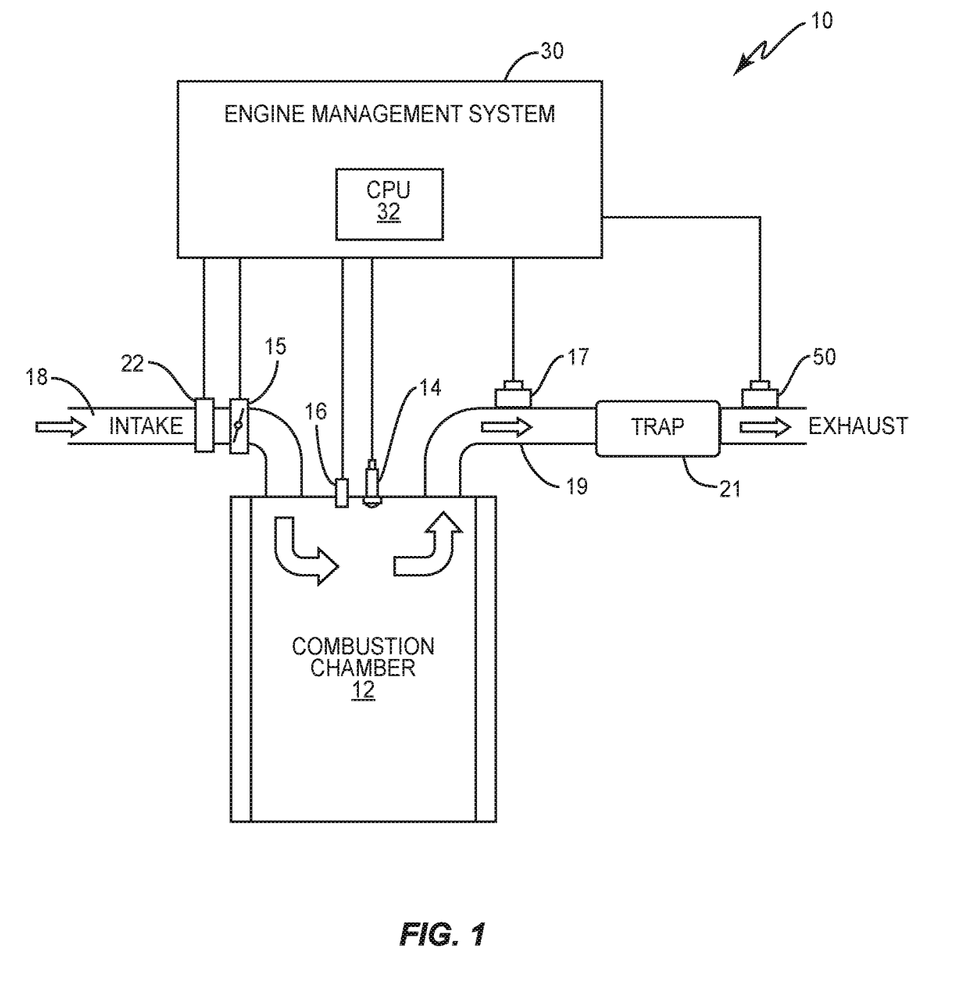
FIG. 1 shows a schematic representation of an engine, having a NOx sensor of the present invention and/or where the method of the one or more embodiments of the present invention may be implemented.

FIG. 1 shows a schematic of an exemplary internal combustion engine 10, which may be of any type (e.g., piston, rotary, nutating disk, etc.). The engine 10 includes at least one combustion chamber 12 with associated piston, valves, etc. (not shown), an intake plenum 18, an exhaust plenum 19, and an engine management system 30. The intake plenum 18 supplies air to the combustion chamber 12. A mass airflow (MAF) sensor or manifold air pressure (MAP) sensor 22, advantageously with associated temperature sensor, is disposed in the intake plenum 18 so that the incoming air conditions may be monitored as the airflow changes due to the opening or closing of the throttle body 15, which is used to control the load/speed of the engine, typically based on operator demand. A controllable fuel metering system, such as a fuel injector 16, supplies fuel to the combustion chamber under control of the engine management system 30. For diesel engines, the fuel injector 16 typically sprays fuel directly into the combustion chamber 12, and ignition takes place as a result of reaching a particular compression level. For spark ignition engines, the fuel injector 16 may spray fuel into the intake plenum 18 or directly into the combustion chamber 12, and a spark ignition device 14, e.g., spark plug, operates under the control of the engine management system 30 to ignite the air and fuel mixture in the combustion chamber 12 at the desired time in the cycle for proper combustion. A NOx sensor 50 is disposed in the exhaust plenum 19, downstream of a NOx trap 21 to sense the amount of NOx in the exhaust gases. Note that the NOx trap 21 may be placed in any appropriate location in the exhaust plenum. The engine management system 30 includes one or more processing circuits 32 (or, "processing circuitry" 32, collectively "controller") that control the fuel supply amount and timing, ignition timing, and other engine parameters based on the input from various sensors and the programming of the processing circuits 32. For example, the engine management system 30 uses the NOx sensor 50, as described below, to help control the urea injector 17 so that the engine 10 operates with desired exhaust conditions. As can be appreciated, the controller 32 may be a centralized microprocessor, or may be a distributed architecture, where different portions of the controller 32, which may be physically distributed, handle different engine functions, such as the computations and signaling associated with the NOx sensor 50, with suitable hardware, firmware, and/or software programming to carry out the functions described herein. Other than the particulars of the NOx sensor 50 and the operation of the processing circuit(s) 32 related to the NOx sensor 50, described in greater detail below, the configuration and operations of the engine 10 are well known to those of skill in the art, and are not discussed further herein in the interests of brevity.

Figure 2:
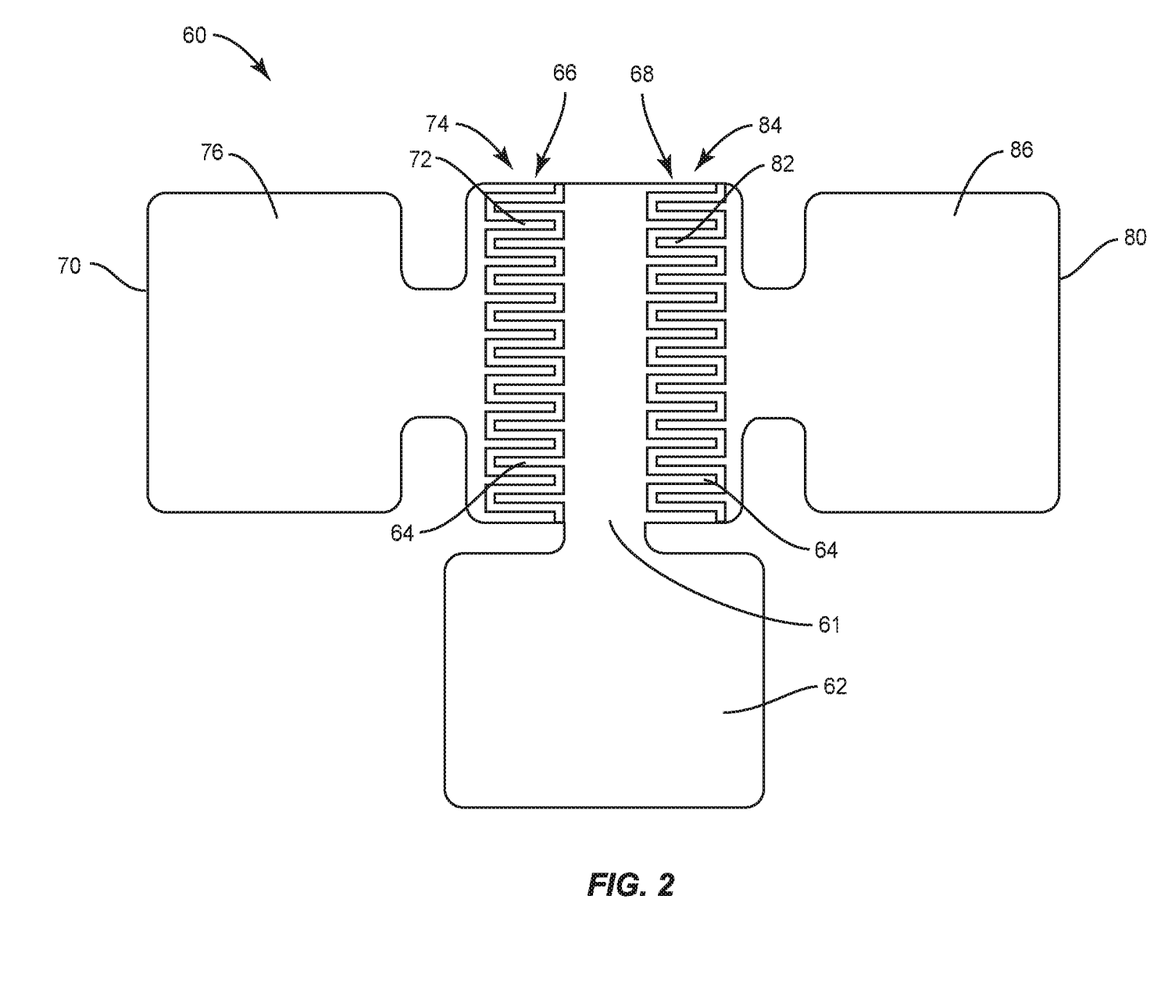
FIG. 2 shows a schematic representation of the electrode configurations of one embodiment of a NOx sensor.
Figure 3:
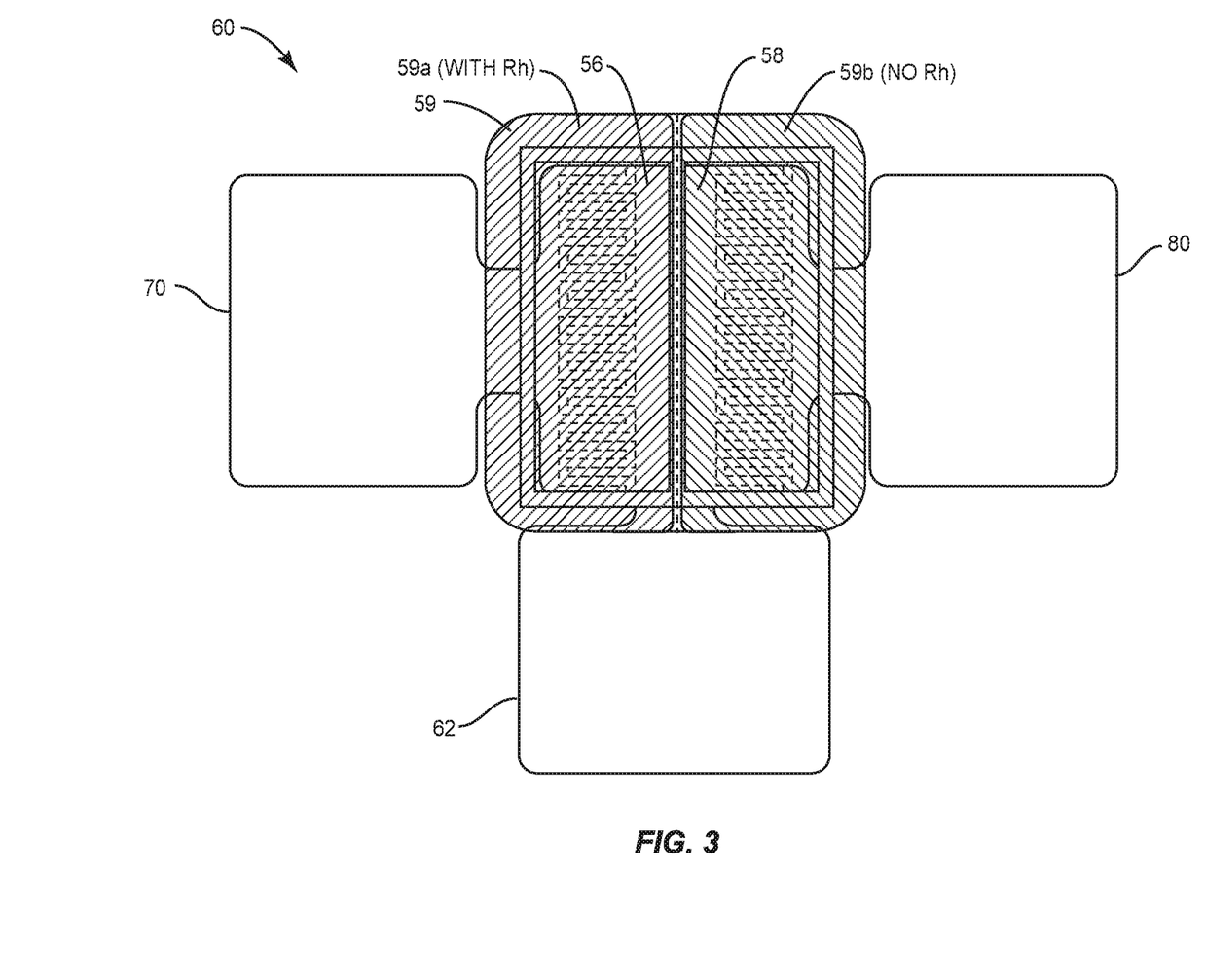
FIG. 3 shows the apparatus of FIG. 2 with the addition of the MOS layer and the differing porous protective (catalytic filter) layers.
Figure 4:
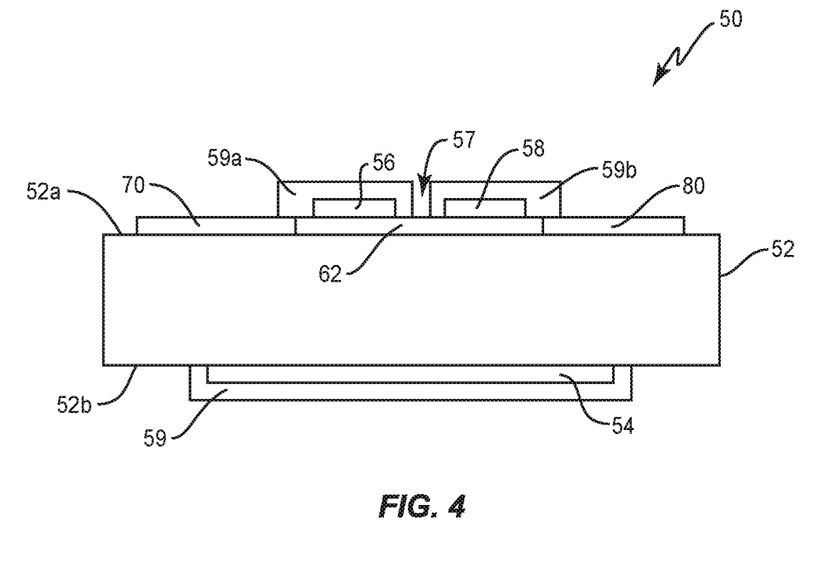
FIG. 4 shows a side view of the apparatus of FIG. 3.

Referring now to FIGS. 2-4, the NOx sensor 50 may be a resistive based NOx sensor, with an exhaust/NOx sensing portion 60 mounted to a dielectric substrate 52. The dielectric substrate 52 may be a fired ceramic dielectric substrate of any suitable type known in the semiconductor art. The NOx sensor 50 may or may not include a resistance based heater portion 54 (see FIG. 4), also mounted to the dielectric substrate 52, but in spaced relation to the sensing portion 60.

In some embodiments, the sensing portion 60 includes a common electrode 62, a first sensing electrode 70, and a second sensing electrode 80, all disposed on a first or top side 52a of the dielectric substrate 52. The common electrode 62 includes a central area 61 and two sets of fingers 64, each set including a plurality of fingers that form respective combs 66,68. The combs 66,68 may advantageously extend in opposite lateral directions from the central area 61, although this is not required. For the configuration shown in FIGS. 2-4, the first sensing electrode 70 is disposed on one lateral side of the common electrode 62 in spaced relation thereto. The first sensing electrode 70 includes a set of a plurality of fingers 72 that form a comb 74, and a terminal area 76. The comb 74 of the first sensing electrode 70 is advantageously intermeshed with comb 66 of the common electrode 62 to form a comb structure, with the respective fingers 64,72 being spaced from each other by a gap so that there is not direct contact between the two electrodes 62,70. Likewise, the second sensing electrode 80 is disposed on the opposite lateral side of the common electrode 62 from the first sensing electrode 70, and in spaced relation to the common electrode 62. The second sensing electrode 80 includes a plurality of fingers 82 that form a comb 84, and a terminal area 86. The comb 84 of the second sensing electrode 80 is advantageously intermeshed with comb 68 of the common electrode 62 to form another comb structure, with the respective fingers 64,82 being spaced from each other by a gap so that there is not direct contact between the two electrodes 62,80. Further, there is no direct contact between the first and second sensing electrodes 70,80. Note that the electrodes 70,80 are electrically conductive, and may be formed of any suitable material, such as platinum or palladium or other suitable refractory conductor. Note that the length and spacing of the fingers 64,72,82 of combs 66,68,74,84, and their particular materials, may be adjusted as desired for the particular operating conditions for the NOx sensor 50.

An n-type (e.g., $TiO_2$) or p-type (e.g., $Cr_2O_3$) metal oxide semiconductor (MOS) layer 56 is placed over combs 66,74 so that the layer 56 forms a semiconductor bridge between the first sensing electrode 70 and the common electrode 62. Likewise, an n-type or p-type metal oxide semiconductor layer 58 is placed over combs 68,84 so that the layer 58 forms a semiconductor bridge between the second sensing electrode 80 and the common electrode 62. Note that MOS layer 56 and MOS layer 58 should have identical material composition and optionally geometries (other than being potential mirror images of each other), and therefore be of the same type (i.e., p-type or n-type), and isolated from each other (no contact, e.g., with a gap between them). The layers 56,58 are advantageously sintered to their respective electrodes 62,70,80 to ensure good physical and electrical contact. Relevant to the discussion below, it should be understood that an n-type semiconductor has a resistance that is significantly lower and has a positive relationship with oxygen content when exposed to exhaust gases from a combustion process operating in the rich region, while the resistance is orders of magnitude higher and may be relatively uncorrelated to the oxygen content in the lean region. Conversely, a p-type semiconductor has a resistance that is significantly lower and has a negative relationship with oxygen content when exposed to exhaust gases from a combustion process operating in the lean region, while the resistance is orders of magnitude higher and may be relatively uncorrelated to the oxygen content in the rich region.

Respective porous dielectric protective coating layers 59a,59b are placed over the semiconductor layers 56,58, and neighboring portions of the electrodes 62,70,80. These porous dielectric protecting coating layers 59a,59b may sometimes be referred to herein as catalytic filter layers 59a,59b. These catalytic filter layers 59a,59b are distinct from each other and are therefore separated by a corresponding gap 57. Note that the "gaps" described herein, including gap 57 may be empty voids, the gaps can alternatively be entirely/partially filled with suitable material, such as a dielectric frit or glaze material, as is desired. Both catalytic filter layers 59a,59b may include catalytic precious metal(s), such as platinum, and/or palladium, as well as oxygen storage components such as cerium oxide or other suitable material as may be necessary to achieve the desired functional characteristics of the sensing portion 60. These catalytic materials may be an initial part of the composition of the catalytic filter layers 59a,59b, or added as to impregnate the catalytic filter layers 59a,59b in a subsequent operation. In addition, one of the catalytic filter layers, for example coating layer 59a, contains Noxcat material (at a defined level, such as 0.25% to 2.5%), while the other catalytic filter layers (in this example 59b) is substantially free of the Noxcat material. Substantially free, in this context, means that the concentration of the Noxcat material is approximately zero, and at least low enough not to convert any substantial amounts of NOx to $N_2$ and $O_2$, so as to not substantially change the resistance of the associated MOS layer due to the presence of NOx in the exhaust gas (as compared to an identical exhaust gas without the NOx).

Referring to FIGS. 4-5, a first oxygen sensing circuit 42 is formed by the common electrode 62, the MOS layer 56, the first sensing electrode 70. The first oxygen sensing circuit 42 includes the MOS layer 56 having the catalytic filter layer 59a of a first type, and is therefore associated with the catalytic filter layer 59a of the first type. A second oxygen sensing circuit 44 is formed by the common electrode 62, the MOS layer 58, the second sensing electrode 80. The second oxygen sensing circuit 44 includes the MOS layer 58 having the catalytic filter layer 59b of a second type, and is therefore associated with the catalytic filter layer 59b of the second type. In an illustrative example, the catalytic filter layer of the first type comprises Noxcat material, while the catalytic filter layer of the second type is substantially Noxcat material free. In another illustrative example, the catalytic filter layer of the first type is substantially Noxcat material free, and the catalytic filter layer of the second type comprises Noxcat material.

When Noxcat material is present in the catalytic filter layer (e.g. 59a), and that catalytic filter layer is exposed to the exhaust stream having NOx present, the Noxcat material interacts with NOx to produce $N_2$ and $O_2$. Thus, in an example where the MOS layer 56 is covered by the porous catalytic filter layer with Noxcat material (59a), while MOS layer 58 is covered by a porous catalytic filter layer that is substantially Noxcat material free (59b), MOS layer 56 responds, when NOx is present in the exhaust plenum 19 at the location of the NOx sensor 50, in a way so as to indicate a higher oxygen level than the MOS layer 58 covered by the porous layer without Noxcat material (59b). For example, when MOS layers 56,58 are both n-type semiconductors, then MOS layer 56 has a significantly higher resistance than MOS layer 58, when, in the absence of NOx, the two layers 56,58 would have substantially similar resistances. Therefore, despite being exposed to a common exhaust having a certain (and shared) actual oxygen level, the two sensor circuits 42,44 provide different resistances, with the difference in resistance proportional to the amount of NOx present in the exhaust plenum 19 after the NOx trap 21.

In some, but not all, embodiments, an optional heater portion 54 is advantageously disposed on the bottom side 52b of the dielectric substrate 52, generally opposite from the exhaust sensing portion 60. See FIG. 4. In other embodiments (not shown), the heater portion 54 may be disposed on the same side 52a of the dielectric substrate 52 as the exhaust sensing portion 60, provided the two portions 54, 60 are electrically isolated (not electrically connected other than through ground). This can be achieved by applying a dielectric layer (not shown) over the heater portion 54 via screen printing, vapor deposition, or other techniques known in the art. In still other embodiments, the heater portion 54 is omitted. The heater portion 54 may take any suitable form and may be formed of any suitable material such as tungsten, platinum, palladium, other precious metals, ceramic (such as silicon nitride $Si_3N_4$), or other materials known in the art. Referencing FIGS. 4-5, the heater portion 54 may be advantageously connected to ground and to a voltage source, such as a twelve volt DC voltage source $VS_1$. The heater portion 54 may also have a suitable protective and/or electrically insulating layer 59, as desired.

The NOx sensor 50 may have suitable connections for power and other signals. For example, in some embodiments, the NOx sensor 50 has four contacts or leads 55, 69, 79, 89 for making suitable connections. Lead 55 is electrically connected to the heater portion 54, and functions as a power (+) lead for the heater portion 54. Lead 69 is electrically connected to the common electrode 62, and acts as a ground (−) lead for the sensing portion 60. Lead 79 is electrically connected to the first sensing electrode 70, and acts as the output from first sensing circuit 42. Lead 89 is electrically connected to the second sensing electrode 80, and acts as the output from second sensing circuit 44. Lead 69 may also function as a ground lead for heater portion 54, or there may be an additional lead (not shown) for a separate ground lead for heater portion 54.

Together, the NOx sensor 50 and the controller 32 form a nitrous oxide sensing assembly or system 5. In some embodiments, the NOx sensor assembly 5 is such that the NOx sensor 50 is connected directly to the controller 32 so that the sensed oxygen level data from the NOx sensor 50 is supplied to the controller 32. In other embodiments, the NOx sensor assembly 5 includes a connecting circuit 90 that interconnects the NOx sensor 5 to the computational portions of controller 32. See FIG. 5. Note that the connecting circuit 90, if present, may be a sub-portion of the controller 32, be a separate component or components between the NOx sensor 50 and the controller 32, or dispersed in any suitable manner. In one or more illustrative embodiments, the connecting circuit 90 includes voltage source $VS_1$, which may be, as illustrated, a twelve volt DC voltage source.

Voltage source $VS_1$ connects to one side of heater portion 54 via shunt resistor $R_{HS}$ and lead 55. Suitable leads disposed on either side of shunt resistor $R_{HS}$ allow the voltage drop $V_{HS}$ across shunt resistor $R_{HS}$ to be measured. Note that the line $L_{VHS}$ for $V_{HS}$, as with other voltage drop lines herein, is illustrated and discussed as being a single line merely for the sake of simplicity, but are typically two lines each. The opposing end of heater portion 54 connects to ground via lead 69.

The connecting circuit 90 also includes a constant voltage source CV, which will be assumed to be powered using a nominal voltage of five volts or any other suitable stable power source that is available. The constant voltage source CV connects to the first sensing circuit 42 via resistors $R_1$ and $R_2$ and lead 79. As can be appreciated, resistors $R_1$ and $R_2$ form a first voltage divider, with the voltage drop $V_2$ across resistor $R_2$ measured and provided by line $L_{V2}$. The sensing circuit 92 is completed to ground via the first sensing circuit 42 (e.g., first sensing electrode 70, MOS layer 56, and common electrode 62). The current through the sensing circuit 92 is represented by $I_a$ in FIG. 5. The constant voltage source CV connects to the second sensing circuit 44 via resistors $R_3$ and $R_4$ and lead 89. As can be appreciated, resistors $R_3$ and $R_4$ form a second voltage divider, with the voltage drop $V_4$ across resistor $R_4$ measured and provided by line $L_{V4}$. The sensing circuit 94 is completed to ground via second sensing circuit 44 (e.g., sensing electrode 80, semiconductor layer 58, and common electrode 62). The current through the sensing circuit 94 is represented by $I_b$ in FIG. 5. Note that in alternate embodiments, resistor $R_1$ and/or resistor $R_3$ may be omitted from their respective circuits, or additional resistors may be added to their respective circuits for scaling or calibration purposes.

The connecting circuit 90 provides voltage drop $V_2$ to the controller 32 via line $L_{V2}$, voltage drop $V_{HS}$ to controller 32 via line $L_{VHS}$, the actual voltage $V_S$ of voltage source $VS_1$ to controller 32 via line $L_{VS}$, and voltage drop $V_4$ to the controller 32 via line $L_{V4}$.

The controller 32 may determine the NOx level based on the voltage levels supplied to it by the sensing circuits 42,44. In particular, the controller 32 may determine the voltage difference between $V_2$ and $V_4$, and then determine the NOx level based thereon, advantageously taking into account the temperature of the NOx sensor 50.

The temperature of the NOx sensor 50 may be determined by controller 32 based on the resistance of the heater portion 54. For example, the current $I_H$ in the heater portion 54 may be calculated as the voltage drop $V_{HS}$ across the shunt resistor $R_{HS}$, divided by the resistance of the shunt resistor $R_{HS}$, or $I_H = V_H S/R_{HS}$. Then, the resistance $R_H$ of the heater portion 54 may be calculated based on the voltage drop across the heater portion 54 divided by the current $I_H$ through the heater portion 54. Thus, $R_H$ may be calculated as $R_H = (V_S - V_{HS})/I_H$. Then, using $R_H$, temperature T may be calculated using a suitable formula, for example T=(M× $R_H$)+B, where the slope M and the constant B are dependent on the heater portion 54 design. As can be appreciated, M and B can be determined in a calibration process, and the relevant values stored in memory of the engine management system 30 for use by the controller 32.

The controller 32 receives the inputs derived from the NOx sensor 50 and other sensors, and advantageously controls the operation of the urea injector 17, and optionally other functions such a fuel metering, ignition timing, and other engine functions.

The discussion above has generally been in the context of the temperature of the NOx sensor 50 being derived from the resistance of the heater portion 54 that is part of the NOx sensor 50. Thus, the heater portion 54 fills two roles: heating the NOx sensor 50 and sensing temperature thereof. However, in some embodiments, a temperature sensor distinct from the heater portion 54 may alternatively employed. Thus, the NOx sensor 50 may include a thermocouple or other suitable temperature sensing device 51, in addition to the exhaust sensing portion 60 and the optional heater portion 54. Such a temperature sensor 51 is shown in FIG. 5 in dashed lines to indicate its optional presence, with its connection line to controller 32 not shown for simplicity. And, the temperature of the NOx sensor 50 may be determined by controller 32 based on data from the temperature sensor 51 in a conventional fashion, either as an alternative or in addition to determining the temperature based on the resistance of the heater portion 54.

Figure 6:
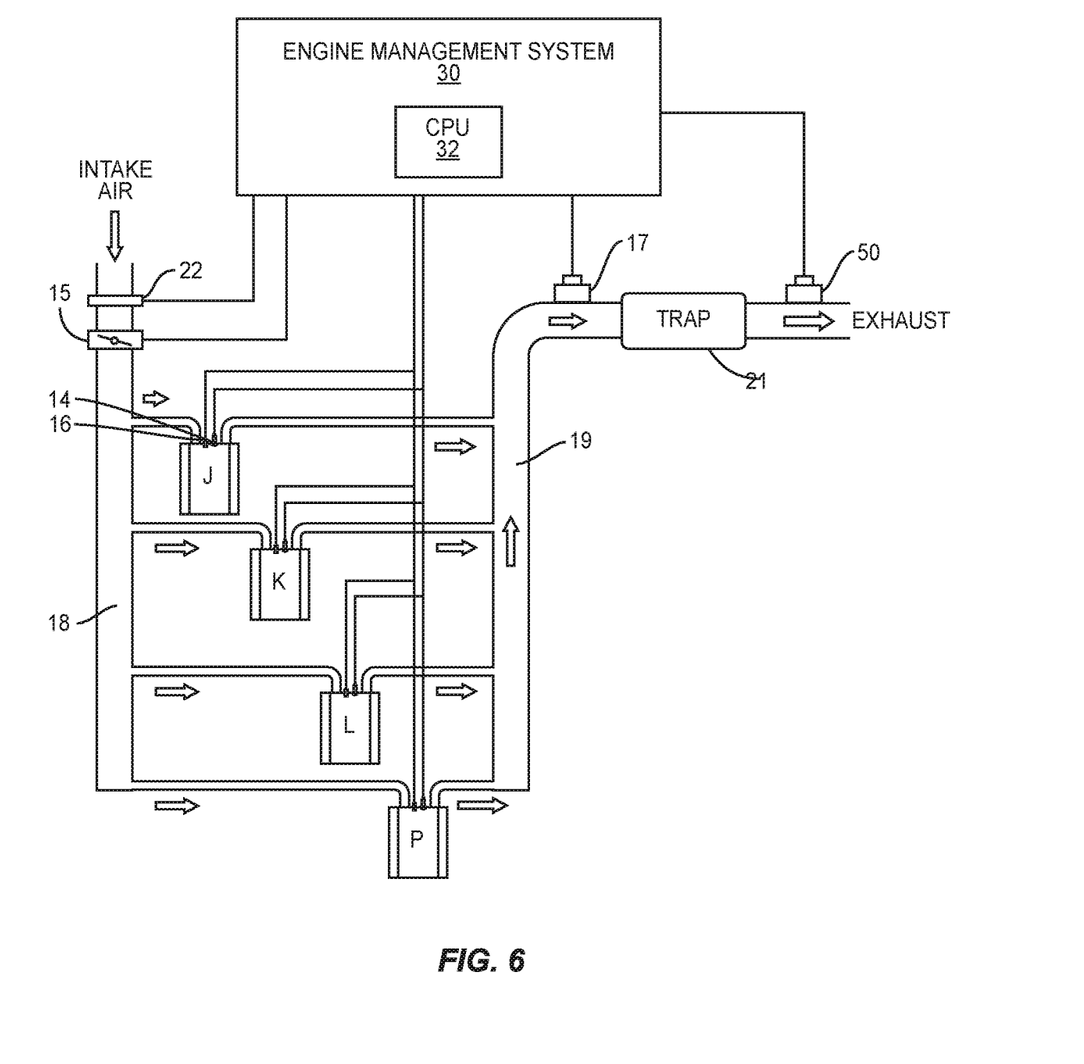
FIG. 6 shows one multiple-cylinder configuration with a common NOx sensor for all cylinders.

The discussion above has generally been in the context of controlling an engine 10 having a single cylinder/combustion chamber. However, a similar approach may be used with engines having multiple cylinders, such as that shown in FIG. 6 with cylinders J, K, L, and P. In FIG. 6, a single common NOx sensor 50 is used for multiple cylinders.

The discussion above has generally been in the context of an internal combustion engine; however, the present invention is not limited in application to internal combustion engines. Indeed, the NOx sensing method described above can be used to control NOx reduction processes generally. Thus, for example, the method(s) described herein may be used for NOx measurement and NOx reduction in combustion processes in a furnace or a water heater. As with the engine-based discussion above, the NOx sensor 50 is disposed so as to sense exhaust gases in the exhaust plenum 19 from the combustion process.

Figure 7:
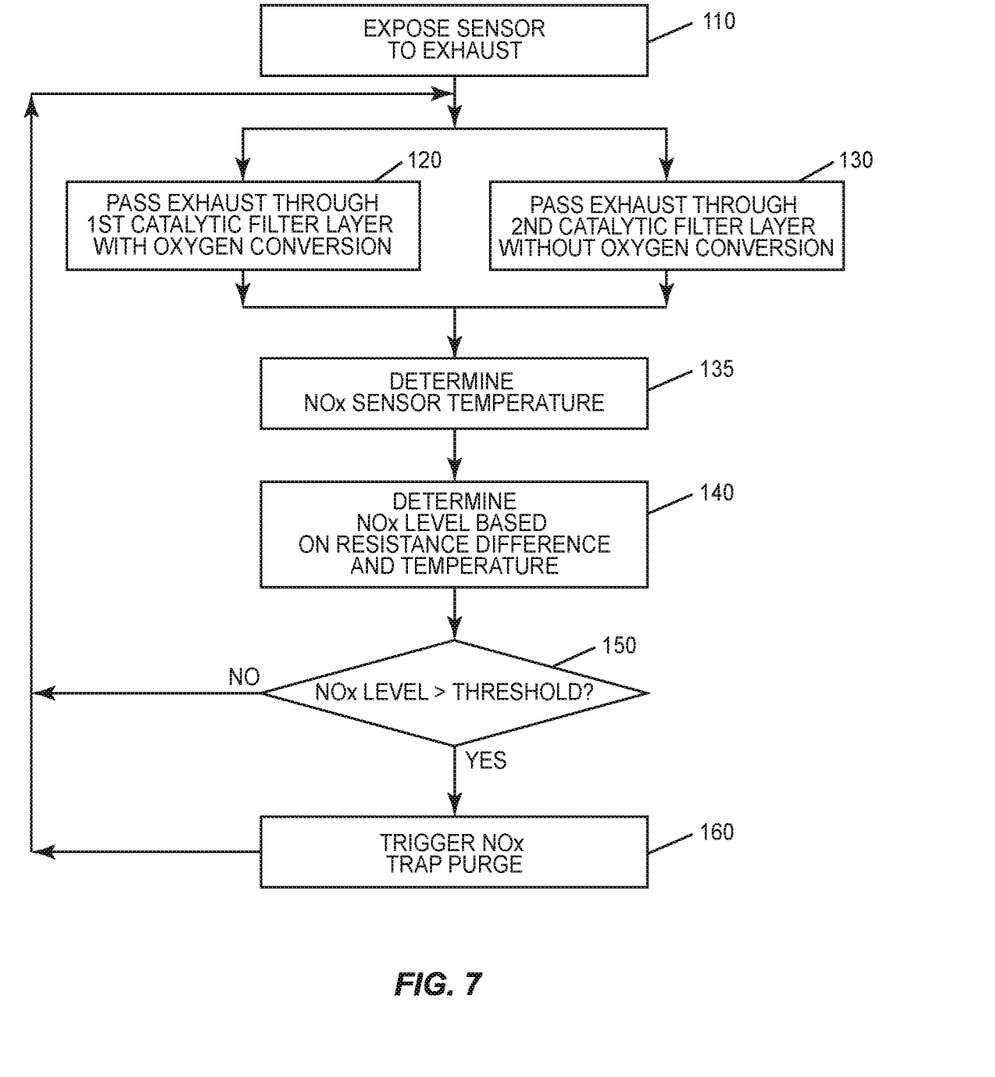
FIG. 7 shows an exemplary process flow for one or more aspects.

From the above, it can be seen that the NOx sensor 50 may be used to detect nitrous oxide in exhaust from a combustion process. For example, as shown in FIG. 7, one method for detecting nitrous oxide in exhaust from a combustion process is to expose the NOx sensor 50 to the exhaust from the combustion process (step 110). As discussed above, the NOx sensor 50 has first and second oxygen sensing circuits 42,44 that share a common electrode 62; wherein the first oxygen sensing circuit 42 comprises a first metal oxide semiconductor portion 56 in contact with the common electrode 62; wherein the second oxygen sensing circuit 44 comprises a second metal oxide semiconductor portion 58 in contact with the common electrode 62. Some of the exhaust passes through a first catalytic filter layer 59a (step 120) to reach the first metal oxide semiconductor portion 56. Simultaneously, some of the exhaust passes through a second catalytic filter layer 59b (step 130) to reach the second metal oxide semiconductor portion 58. At step 120, nitrous oxide in the exhaust is converted at least partially to oxygen while passing through the first catalytic filter layer 59a prior to reaching the first metal oxide semiconductor portion 56; but during parallel step 130, nitrous oxide in the exhaust is not converted partially to oxygen while passing through the second catalytic filter layer 59b to reach the second metal oxide semiconductor portion 58. The process also includes, at step 135, determining the temperature of the NOx sensor, which may be accomplished in any suitable way, such as calculated from the heater current $I_H$ or the voltage drop across a resistor $R_HS$ disposed in series with the heater portion 54, or be based on data from a separate temperature sensor 51. Note that step 135 may occur before or after or concurrent with step 120 and 130. The process continues, at step 140, with determining a nitrous oxide level in the exhaust based on a resistance differential between the first oxygen sensing circuit 42 and the second oxygen sensing circuit 44 and the determined temperature of the NOx sensor. As pointed out above, the first and second oxygen sensing circuits 42,44 are configured to provide similar resistances when subjected to an environment free of nitrous oxide, but to provide substantially different resistances when subjected to an environment containing nitrous oxide(s). The process may continue to the optional step of comparing the resistance differential to a threshold (step 150), and triggering a purging of the NOx trap 21 (e.g., providing urea/ammonia thereto) (step 160) when the determined NOx level exceeds the threshold. The threshold may advantageously vary based on the determined temperature of the sensor, so as to compensate for the temperature dependent response of the MOS materials of layers 56,58 to the presence of oxygen.

The discussion above has generally been in the context of catalytic filer layer 59a having a particular Noxcat material, while the other catalytic filter layer 59b is substantially free of that particular Noxcat material. Thus, catalytic filer layer 59a may comprise rhodium, while catalytic filter layer 59b is substantially free of rhodium. This is an example using a single Noxcat material, and is believed to be an advantageous configuration. However, in other aspects or embodiments, catalytic filer layer 59a may comprise a combination of multiple Noxcat materials (e.g., rhodium and nickel), while catalytic filter layer 59b is substantially free of those Noxcat materials. Claim language of "wherein the first catalytic filter layer comprises a Noxcat material . . . wherein the second catalytic filter layer is substantially free of the Noxcat material," and the like, is intended to cover both situations (single Noxcat material and combination of two Noxcat materials), and situations where more Noxcat materials are involved.

The methods and engine control systems discussed above provide the opportunity for enhanced combustion and/or engine control so that greater fuel economy and/or reduced emissions may be achieved.

For more information about forming the electrodes 62,70, 80 and the MOS layers 56,58, and the like, and/or temperature compensation of the sensed oxygen levels, see U.S. Patent Application Publication 2014/0130779 and/or U.S. Pat. Nos. 8,586,394 and 8,959,987, the disclosures of which are incorporated herein by reference in their entirety.

The present invention may, of course, be carried out in other specific ways than those herein set forth without departing from the scope of the invention. The present embodiments are, therefore, to be considered as illustrative and not restrictive.

What is claimed is:
1. A nitrous oxide sensor, comprising:
a substrate;
a first oxygen sensing circuit affixed on a first side of the substrate;
a second oxygen sensing circuit affixed on the first side of the substrate;
wherein the first oxygen sensing circuit comprises:
 a first sensing electrode;
 a common electrode;
 a first metal oxide semiconductor portion electrically bridging a first physical gap between the first sensing electrode and the common electrode;
wherein the second oxygen sensing circuit comprises:
 a second sensing electrode;
 the common electrode;

a second metal oxide semiconductor portion electrically bridging a second physical gap between the second sensing electrode and the common electrode;

wherein the first sensing electrode and the common electrode are configured to form a first comb structure; wherein the second sensing electrode and the common electrode are configured to form a second comb structure; wherein both the first and second comb structures are disposed parallel to the first side of the substrate and comprise a plurality of interleaved fingers of the respective sensing electrode and the common electrode;

wherein a first catalytic filter layer is disposed over the first metal oxide semiconductor portion; wherein the first catalytic filter layer comprises a Noxcat material; wherein the Noxcat material is one of rhodium, ruthenium, cobalt, palladium, or nickel;

wherein a second catalytic filter layer is disposed over the second metal oxide semiconductor portion; wherein the second catalytic filter layer is substantially free of the Noxcat material;

wherein the first and second metal oxide semiconductor portions are disposed in spaced relation to each other such that there is a third physical gap between the first and second metal oxide semiconductor portions;

wherein the first and second catalytic filter layers are disposed in spaced relation to each other;

wherein the first and second oxygen sensing circuits are configured to provide similar resistances when subjected to an environment free of nitrous oxide, but to provide substantially different resistances when subjected to an environment containing nitrous oxide(s).

2. The nitrous oxide sensor of claim 1, wherein the Noxcat material is rhodium.

3. The nitrous oxide sensor of claim 1, further comprising a heater portion disposed on a second side of the substrate, the second side opposite the first side.

4. The nitrous oxide sensor of claim 1, wherein the first and second metal oxide semiconductor portions are both n-type semiconductors, or are both p-type semiconductors.

5. The nitrous oxide sensor of claim 1, wherein the first and second sensing electrodes are mirror images of each other.

6. The nitrous oxide sensor of claim 1, wherein the gap is an empty void.

7. A nitrous oxide sensor assembly, comprising:
a nitrous oxide sensor; the nitrous oxide sensor comprising:
a substrate;
a first oxygen sensing circuit affixed on a first side of the substrate;
a second oxygen sensing circuit affixed on the first side of the substrate;
wherein the first oxygen sensing circuit comprises:
a first sensing electrode;
a common electrode;
a first metal oxide semiconductor portion electrically bridging a first physical gap between the first sensing electrode and the common electrode;
wherein the second oxygen sensing circuit comprises:
a second sensing electrode;
the common electrode;
a second metal oxide semiconductor portion electrically bridging a second physical gap between the second sensing electrode and the common electrode;

wherein a first catalytic filter layer is disposed over the first metal oxide semiconductor portion; wherein the first catalytic filter layer comprises a Noxcat material; wherein the Noxcat material is one of rhodium, ruthenium, cobalt, palladium, or nickel;

wherein a second catalytic filter layer is disposed over the second metal oxide semiconductor portion; wherein the second catalytic filter layer is substantially free of the Noxcat material;

wherein the first and second metal oxide semiconductor portions are disposed in spaced relation to each other such that there is a third physical gap between the first and second metal oxide semiconductor portions;

wherein the first and second catalytic filter layers are disposed in spaced relation to each other;

wherein the first and second oxygen sensing circuits are configured to provide similar resistances when subjected to an environment free of nitrous oxide, but to provide substantially different resistances when subjected to an environment containing nitrous oxide(s);

a first voltage divider operatively connected to the first oxygen sensing circuit; and a second voltage divider operatively connected to the second oxygen sensing circuit.

8. A nitrous oxide sensor, comprising:
a substrate;
an electrically conductive common electrode mounted on a first side of the substrate;
an electrically conductive first sensing electrode mounted on the first side of the substrate in spaced relation to the common electrode;
an electrically conductive second sensing electrode mounted on the first side of the substrate in spaced relation to the common electrode;
wherein the common electrode is disposed between the first and second sensing electrodes; wherein the first sensing electrode and the common electrode are configured to form a first comb structure; wherein the second sensing electrode and the common electrode are configured to form a second comb structure; wherein both the first and second comb structures are disposed parallel to the first side of the substrate and comprise a plurality of interleaved fingers of the respective sensing electrode and the common electrode;
a first metal oxide layer semiconductor layer disposed over the first comb structure and forming a first semiconductor bridge between the first sensing electrode and the common electrode;
a second metal oxide semiconductor layer disposed over the second comb structure and forming a second semiconductor bridge interconnecting the second sensing electrode and the common electrode;
wherein the first and second metal oxide semiconductor layers are spaced from each other;
a first catalytic filter layer disposed over the first metal semiconductor oxide layer;
a second catalytic filter layer disposed over the second metal oxide semiconductor layer;
wherein the first catalytic filter layer comprises rhodium and the second catalytic filter layer is substantially rhodium free.

9. The nitrous oxide sensor of claim 8, further comprising a heater portion disposed on a second side of the substrate, the second side opposite the first side.

10. The nitrous oxide sensor of claim 8, wherein the first and second metal oxide layers are n-type semiconductors.

11. The nitrous oxide sensor of claim 8, wherein the first and second metal oxide layers are p-type semiconductors.

12. The nitrous oxide sensor of claim 8, wherein the first and second sensing electrodes are mirror images of each other.

13. A method of detecting nitrous oxide in exhaust from a combustion process, the method comprising:
exposing a nitrous oxide sensor to the exhaust from the combustion process;
wherein the nitrous oxide sensor comprises:
a substrate;
a first oxygen sensing circuit having a first sensing electrode affixed on a first side of the substrate;
a second oxygen sensing circuit having a second sensing electrode affixed on the first side of the substrate;
wherein the first and second oxygen sensing circuits share a common electrode;
wherein the first oxygen sensing circuit comprises a first metal oxide semiconductor portion in contact with the common electrode;
wherein the second oxygen sensing circuit comprises a second metal oxide semiconductor portion in contact with the common electrode;
wherein the first sensing electrode and the common electrode are configured to form a first comb structure; wherein the second sensing electrode and the common electrode are configured to form a second comb structure; wherein both the first and second comb structures are disposed parallel to the first side of the substrate and comprise a plurality of interleaved fingers of the respective sensing electrode and the common electrode;
passing some of the exhaust through a first catalytic filter layer to reach the first metal oxide semiconductor portion, and simultaneously passing some of the exhaust through a second catalytic filter layer to reach the second metal oxide semiconductor portion;
wherein nitrous oxide in the exhaust is at least partially converted to oxygen while passing through the first catalytic filter layer prior to reaching the first metal oxide semiconductor portion, but nitrous oxide in the exhaust is not converted to oxygen while passing through the second catalytic filter layer to reach the second metal oxide semiconductor portion; and
determining a temperature of the nitrous oxide sensor;
determining a nitrous oxide level in the exhaust based on a resistance differential between the first oxygen sensing circuit and the second oxygen sensing circuit and the determined temperature;
wherein the first and second oxygen sensing circuits are configured to provide similar resistances when subjected to an environment free of nitrous oxide, but to provide substantially different resistances when subjected to an environment containing nitrous oxide(s).

14. The method of claim 13, wherein the exposing the nitrous oxide sensor to the exhaust comprises exposing the sensor to the exhaust at a point downstream from a NOx trap.

15. The method of claim 13, further comprising:
comparing the resistance differential to a threshold, the threshold varying based on the determined temperature of the sensor; and
in response to the resistance differential exceeding the threshold, triggering a purging of a NOx trap disposed along an exhaust associated with the combustion process.

16. The method of claim 13, wherein the exposing the nitrous oxide sensor to the exhaust comprises exposing the sensor to the exhaust at a point downstream from a NOx trap.

17. The method of claim 13, further comprising, in response to the resistance differential exceeding the threshold, triggering a purging of a NOx trap disposed along an exhaust associated with the combustion process.

18. The method of claim 13:
wherein the nitrous oxide sensor further comprises a heater portion disposed on a second side of the substrate, the second side opposite the first side;
wherein the determining the temperature of the sensor comprises determining the temperature based on a resistance of the heater portion.

19. The method of claim 13:
wherein the nitrous oxide sensor further comprises a heater portion disposed on a second side of the substrate;
wherein the determining the temperature comprises determining the temperature based on a temperature sensor distinct from the heater portion.

20. The method of claim 13:
wherein the first and second sensing electrodes are mirror images of each other;
wherein the first and second metal oxide semiconductor portions are both p-type semiconductors.

* * * * *